United States Patent [19]

Scodari

[11] Patent Number: 4,457,912
[45] Date of Patent: Jul. 3, 1984

[54] ELECTRIC RAZOR PRESHAVE COMPOSITION

[76] Inventor: Nicholas F. Scodari, P.O. Box 294, R.D. #1, Basking Ridge, N.J. 07920

[21] Appl. No.: 410,960

[22] Filed: Aug. 24, 1982

[51] Int. Cl.³ .......................... A61K 7/15; A61K 7/09; A61K 7/11
[52] U.S. Cl. .......................................... 424/73; 424/71
[58] Field of Search ..................................... 424/71, 73

[56] References Cited

U.S. PATENT DOCUMENTS

| | | | |
|---|---|---|---|
| 3,354,175 | 11/1967 | Fruhstorfer et al. | 424/73 |
| 3,824,303 | 7/1974 | Lanzet et al. | 424/73 |
| 3,953,591 | 4/1976 | Snyder | 424/73 |
| 3,958,581 | 5/1976 | Abegg et al. | 424/71 |
| 4,065,422 | 12/1977 | Lundmark et al. | 424/73 |
| 4,128,631 | 12/1978 | Lundmark et al. | 424/73 |
| 4,240,450 | 12/1980 | Grollier et al. | 424/73 |

FOREIGN PATENT DOCUMENTS 24161 2/1981 European Pat. Off. .............. 424/73

OTHER PUBLICATIONS

Kirk–Othmer, *Encyc. of Chem. Technology*, 2nd Ed., vol. 19, pp. 554–555.
Brochure of EF–KAY Product Co., Inc. (no date).

*Primary Examiner*—Jerome D. Goldberg
*Assistant Examiner*—Freda Abramson
*Attorney, Agent, or Firm*—Ronald A. Schapira

[57] ABSTRACT

An electric razor preshave composition containing an effective amount of a cationic polymer. The cationic polymer is selected so that, when the composition is applied to hair to be shaven, the cationic polymer clings to each individual hair, and when the composition subsequently dries on the hair, the cationic polymer forms a relatively stiff but pliable coating on each hair. The dry cationic polymer coating makes each hair stay relatively erect during shaving and, in addition, neutralizes static charges on the metal blades of an electric razor so that the individual hairs are not repelled by the razor blades as they are being cut.

5 Claims, No Drawings

ELECTRIC RAZOR PRESHAVE COMPOSITION

BACKGROUND OF THE INVENTION

This invention relates to a novel preshave composition and to an improved method of shaving with an electric razor.

Electric razor preshave compositions for facilitating the shaving of hair, such as facial hair, leg hair and underarm hair, are well known. Typically, such compositions have been applied as liquids to the skin and hair shortly before shaving. To aid in shaving, some of these compositions have lubricated the skin, removed oils and moisture from the hair and skin, and/or caused the hair to rise and protrude temporarily from the skin. In order to provide such effects, these compositions have contained some or all of the following ingredients: an alcohol, such as ethyl alcohol, as a vehicle; water; a light oily ester, such as isopropyl myristate or ispropyl palmitate, and/or a liquid silicone, such as a dialkyl polysiloxane, as a lubricating agent; a surfactant such as a polyethylene glycol ester or ether; ad a pilomotor agent. In addition, such compositions have typically contained a fragrance and a coloring agent to improve their customer appeal.

However, known electric razor preshave compositions have been far from satisfactory. The known compositions have not been adapted to make each individual hair stay erect during shaving so that each hair can be cut straight through with an electric razor. Rather, the known compositions have allowed each hair to bend freely during shaving, causing each hair to be either cut on a bias or torn by the blades of the electric razor. This has made the shaves, obtained with such compositions, less close and smooth than has frequently been desired by shavers. This has also made the hair, shaved with such compositions, appear darker. Some of the known electric razor preshave compositions also have tended to leave oily or other unpleasant films on the skin after the hair on the skin has been shaven. Some of these compositions have also tended to leave residues on the shavings which react with the plastic or metal components of the electric razor, cling to the razor components, and/or cause the shavings to cling to the razor components.

SUMMARY OF THE INVENTION

In accordance with this invention, an electric razor preshave composition is provided, comprising: a vehicle; and an effective amount of a cationic polymer; said cationic polymer being adapted so that, when the composition is applied to hair to be shaven, the cationic polymer clings to each individual hair, and when the composition subsequently dries on the hair, the cationic polymer forms a relatively stiff but pliable coating on each hair.

By the use of this composition, each hair remains relatively erect on the skin surface so that each hair can be cut straight through with an electric razor to give a close and smooth shave. The composition leaves no oily or unpleasant film on the shaven skin and leaves no residue on the shavings which could adversely affect the components of the electric razor.

DETAILED DESCRIPTION OF THE INVENTION

The electric razor preshave composition of this invention comprises a cationic polymer. When the composition is applied to skin and hair before shaving, the cationic polymer clings to, and remains on, the surface of each individual hair. When the composition subsequently dries on the skin and hair, the cationic polymer remains on the surface of each hair to form a relatively stiff but pliable coating on each hair. This stiff but pliable coating causes each hair to stay relatively erect on the skin and not to bend freely while it is being cut by the blades of an electric razor. During shaing, the cationic polymer coating on each individual hair also serves to neutralize static charges which build up on the metal blades of an electric razor as the blades cut the hair. Thereby, the individual hair is not repelled by the blades of the electric razor as it is being cut. The result is that each hair can be cut straight through by the blades of an electric razor to give a shave which is closer and smoother than was heretofore possible with an electric razor. In addition, the shaved hair appears less dark when it has been shaven with an electric razor after applying the composition of this invention than, for example, when it has been shaven by being cut on a bias or torn by the blades of an electric razor after applying a heretofore available electric razor preshave composition.

In the composition of this invention, the use of specific cationic polymers is not critical, and numerous well known cationic polymers can be suitably utilized. Among the cationic polymers which can be utilized are the cationic polymers disclosed in U.S. Pat. No. 4,240,450 at columns 4 to 29, said patent being incorporated herein by reference. The preferred cationic polymers of this invention comprise the quaternary ammonium cationic polymers disclosed in U.S. Pat. No. 4,240,450. Among the quaternary ammonium cationic polymers of this invention, as disclosed in U.S. Pat. No. 4,240,450, particularly preferred are:

I. Quaternary ammonium derivatives of cellulose ethers having the formula:

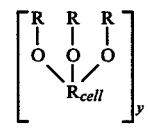

wherein $R_{cell}$ is the radical of an anhydroglucose unit; y is an integer of 50 to 20,000; and each R is a group of the formula:

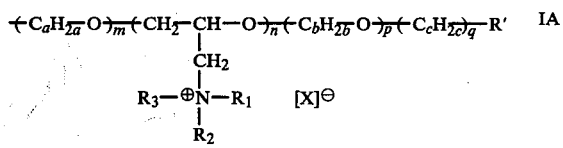

wherein a is the integer 2 or 3; b is the integer 2 or 3; c is the integer 1, 2 or 3; m is 0 or an integer of 1 to 10; n is 0 or the integer 1, 2 or 3; p is 0 or an integer of 1 to 10; q is 0 or 1; R' is a group of the formula:

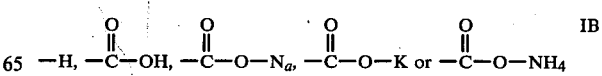

provided that R' is hydrogen when q is 0; $R_1$, $R_2$ and $R_3$, taken individually, is each an alkyl, aryl, aralkyl, alkaryl, cycloalkyl, alkoxyalkyl or alkoxyaryl radical containing up to 10 carbon atoms, provided that, when $R_1$, $R_2$ or $R_3$ is an alkoxyalkyl radical, there are at least 2 carbon atoms separating the oxygen atom from the nitrogen atom and also provided that the total number of carbon atoms present in $R_1$, $R_2$ and $R_3$ is from 3 to 12; or $R_1$, $R_2$ and $R_3$, taken together, are, together with the nitrogen atom to which they are linked, one of the following radicals: pyridine, alphamethylpyridine, 3,5-dimethylpyridine, 2,4,6-trimethylpyridine, N-methylpiperidine, N-ethylpiperidine, N-methylmorpholine or N-ethylmorpholine; X is a cosmetically acceptable anion such as an acetate, borate, bromide, chloride, citrate, tartrate, bisulphate, bisulphite, sulphate, phosphate or succinate; the mean value of n per anhydroglucose unit of this cellulose ether is from 0.01 to 1; and the mean value of (m+n+p+q) per anhydroglucose unit of this cellulose ether is from about 0.01 to 4.

Among the preferred quaternary ammonium cationic polymers of formula I are polymers of hydroxyethyl cellulose reacted with epichlorohydrin and quaternized with trimethyl amine such as are referred to by the name "Quaternium 19" in the *Cosmetic Ingredient Dictionary* and are available from Union Carbide Corporation, Danbury, Conn. under the trademarks "JR-125", "JR-400" and "JR-30M".

II. Quaternary ammonium polymers which are soluble in water, which have a molecular weight of 20,000 to 3,000,000, and which are ether: A. Homopolymers containing, as the main constituent of the chain, units of the formula:

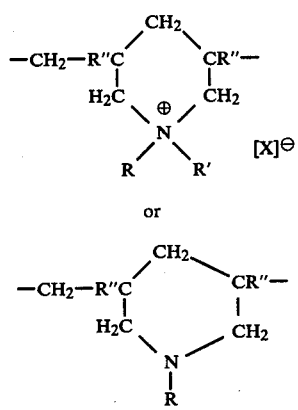

wherein R″ is hydrogen or methyl; R and R′, independently of one another, are an alkyl group having 1 to 22 carbon atoms, a hydroxyalkyl group in which the alkyl group preferably has 1 to 5 carbon atoms or a lower amidoalkyl group; R and R′ are, together with the nitrogen atom to which they are linked, a heterocyclic group such as piperidinyl or morpholinyl; and X is a cosmetically acceptable anion such as an acetate, borate, bromide, chloride, citrate, tartrate, bisulphate, bisulphite, sulphate, phosphate or succinate; or B. Copolymers of acrylamide or diacetone-acrylamide with monomers which provide units corresponding to the units of formula II.

Among these quaternary ammonium polymers, the preferred polymers include: the homopolymer of dimethyldialkylammonium chloride which is referred to by the name "Quaternium 40" in the *Cosmetic Ingredient Dictionary*, is sold under the trademark "MERQUAT 100" by Merck & Co., Rahway, N.J., and has a molecular weight of less than 100,000; and the copolymer of dimethyldialkylammonium chloride and of acrylamide which has a molecular weight of more than 500,000, is referred to by the name "Quaternium 41" in the *Cosmetic Ingredient Dictionary* and is sold under the trademark "MERQUAT 550" by Merck & Co.

III. Quaternary ammonium polymers derived from acrylic or methacrylic acid, which are either: A. Homopolymers containing recurring units of the formula:

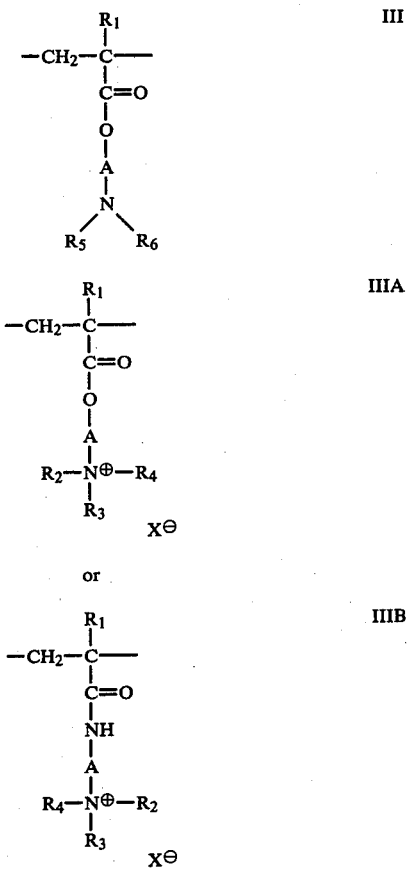

wherein $R_1$ is hydrogen or methyl; A is a linear or branched alkyl group having 1 to 6 carbon atoms or a hydroxyalkyl group having 1 to 4 carbon atoms; $R_2$, $R_3$ and $R_4$ are identical or different and are an alkyl group having 1 to 18 carbon atoms or benzyl; and $R_5$ and $R_6$ are hydrogen or an alkyl group having 1 to 6 carbon atoms; and X is a halogen or methosulphate; or B. Copolymers of monomers which provide units corresponding to the units of formula IIIA or IIIB with acrylamide, methylacrylamide, diacetone-acrylamide or acrylamide or methacrylamide substituted on the nitrogen by lower alkyls, alkyl esters of acrylic or methacrylic acids, vinylpyrrolidone or vinyl esters.

Among these quaternary ammonium polymers, the preferred polymers include: the copolymers of acrylamide and beta-methacryloyloxyethyltrimethylammonium methosulphate sold under the trademark "Reten 205", "Reten 210", "Reten 220" and "Reten 240" by Hercules Chemical Company, Inc., New York, N.Y.; the copolymer of ethyl methacrylate, oleyl methacrylate and beta-methacryloyloxydiethylmethylammonium methosulphate referred to by the name "Quaternium 38" in the *Cosmetic Ingredient Dictionary*; the copolymer of ethyl methacrylate, abietyl methacrylate and beta-methacryloyloxydiethylmethylammonium methosulphate referred to by the name "Quaternium 37" in the *Cosmetic Ingredient Dictionary*; the polymer of beta-methacryloyloxyethyltrimethylammonium bromide referred to by the name "Quaternium 49" in the *Cosmetic Ingredient Dictionary*; the copolymer of beta-methacryloyloxyethyltrimethylammonium methosulphate and beta-methacryloyloxystearyldimethylammonium methosulphate referred to by the name "Quaternium 42" in the *Cosmetic Ingredient Dictionary*; and the copolymer sold under the trademark "Catrex" by National Starch & Chemical Corp., Bridgewater, N.J.

IV. Copolymers of vinylpyrrolidone having recurring units of the formulae:

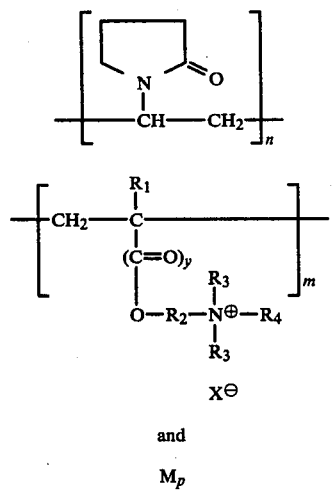

and $M_p$      IVB wherein n is 20 to 99 and preferably 40 to 90 mol %; m is 1 to 80 and preferably 5 to 40 mol %; p is 0 to 50 mol %; (n+m+p) is 100 mol %; $R_1$ is hydrogen or methyl; y is 0 or 1; $R_2$ is —$CH_2$—CHOH—$CH_2$— or —$C_xH_{2x}$—; x is an interger of 2 to 18; $R_3$ is methyl, ethyl or benzyl; $R_4$ is methyl or ethyl; X is Cl, Br, I, $\frac{1}{2}SO_4$, $HSO_4$ or $CH_3SO_3$; and M is a monomeric unit resulting from heteropolymerization using a selected copolymerizable vinyl monomer.

Among these copolymers of the units of formulae IV, IVA and IVB, the preferred copolymers have molecular weights of about 100,000 to 1,000,000 such as the copolymers formed by the reaction of dimethyl sulfate, vinyl pyrrolidone and dimethylaminoethylmethacrylate referred to by the name "Quaternium 23" in the *Cosmetic Ingredient Dictionary* and sold under the trademarks "Gafquat 734" and "Gafquat 755" by GAF Corp., New York, N.Y.

The electric razor preshave composition of this invention also comprises a conventional lower alkyl alcohol, such as ethyl or isopropyl alcohol, as a vehicle. The composition can further comprise water that is preferably added to the alcohol vehicle in an amount sufficient to avoid the extreme "bite" reaction of skin to the alcohol. The composition can still further comprise: a conventional alcohol or water soluble fragrance, such as a conventional musk, citrus or lavender type fragrance; and a conventonal alcohol or water soluble coloring agent, such as FD+C #1 blue or D+C #5 green. If desired, the composition can also include a conventional pilomotor agent such as menthol. In this regards, the use of a pilomotor agent like menthol is preferred in compositions for closely shaving relatively heavy and/or dense hair.

In the electric razor preshave composition of this invention, specific amounts of the individual ingredients are not critical. However, the composition should contain an effective amount of the cationic polymer to form a relatively stiff but pliable, dry coating on individual hairs, to be shaven, that will: (a) keep each hair relatively erect on the skin while it is being shaven; and (b) at least partially neutralize static charges generated on the metal blades of an electric razor, as the blades cut the hair, so that the hair is not repelled by the blades during shaving.

The electric razor preshave composition of this invention preferably comprises about 0.1 to 2.0% (by weight) cationic polymer; about 70 to 95% alcohol; about 5 to 30% water; and about 0.1 to 2% fragrance. This composition can, if desired, also contain about 0.1 to 0.5% of a pilomotor agent such as menthol. However, the composition can also contain significantly greater or lesser percentages of each ingredient. For example, the composition can contain no water, but this would cause the "bite" reaction of the skin. The composition can also comprise up to about 50% water, but this would increase significantly the time required for the composition to dry on the hair and skin, to be shaven.

One example of an electric razor preshave composition of this invention comprises simply: 75% (by weight) ethyl alcohol, 0.50% Quaternium-23, 0.50% Quaternium-40, 23% deionized water and 1% fragrance. This composition can be suitably used to obtain a close and smooth shave of a beard with an electric razor. In this regard, one can apply the composition to the face until the face and the facial hair are wet and then wait a few seconds until the composition has dried on the face so that the individual facial hairs are coated with the dry cationic polymer. Then, the facial hair can be cut with a conventional electric razor. During shaving, the facial hair remain erect while being cut straight through by the electric razor blades so that the face is left smooth and clean. No oily or unpleasant film is left on the face after it has been shaven, and the shavings contain no residue which can react with the material of the electric razor or cling to the parts of the razor.

It is thought that the invention and many of its attendant advantages will be obvious from the foregoing description and it will be apparent that various changes may be made in the electric razor preshave composition and its ingredients without departing from the spirit and scope of the invention or sacrificing all of its material advantages, the composition and process for shaving with the composition, hereinbefore described, being merely preferred embodiments thereof.

I claim:
1. In a method for shaving hair with an electric razor after applying a preshave composition to the hair, the improvement wherein the preshave composition, which is applied, comprises:
a lower alkyl alcohol as a vehicle; and
an effective amount of a quaternary ammonium cationic polymer which can cling to each individual hair to be shaven when the preshave composition is applied to the hair and which can form a relatively stiff but pliable coating on each hair when the preshave composition subsequently dries on each hair.

2. The method of claim 1 wherein the preshave composition comprises about 0.1 to 2.0 weight percent of the cationic polymer.

3. The method of claim 1 wherein the lower alkyl alcohol vehicle is ethyl alcohol or isopropyl alcohol.

4. The method of claim 3 wherein the preshave composition comprises about 70 to 95 weight percent of the lower alkyl alcohol vehicle.

5. The method of claim 4 wherein the preshave composition further comprises about 5 to 30 weight percent of water.

* * * * *